United States Patent
Zhou et al.

(10) Patent No.: US 7,888,663 B2
(45) Date of Patent: Feb. 15, 2011

(54) PLASMONIC STRUCTURE LENS AND ITS APPLICATION FOR ONLINE INSPECTION

(75) Inventors: Wei Zhou, Singapore (SG); Yongqi Fu, Singapore (SG); Enk Ng Lim, Singapore (SG)

(73) Assignee: Nanyang Technological University, Singapore (SG)

( * ) Notice: Subject to any disclaimer, the term of this patent is extended or adjusted under 35 U.S.C. 154(b) by 477 days.

(21) Appl. No.: 12/103,777

(22) Filed: Apr. 16, 2008

(65) Prior Publication Data

US 2009/0261250 A1    Oct. 22, 2009

(51) Int. Cl.
G02B 13/14    (2006.01)
(52) U.S. Cl. .................. 250/504 R; 359/355
(58) Field of Classification Search ............ 250/504 R; 359/355, 738
See application file for complete search history.

(56) References Cited

U.S. PATENT DOCUMENTS 7,301,263 B2 *  11/2007  Maldonado et al. ..... 313/103 R
2008/0252894 A1 * 10/2008  Lakowicz et al. ........... 356/445
2010/0141939 A1 *  6/2010  Zhan ........................ 356/301

OTHER PUBLICATIONS

Y.Fu, W.Zhou, L. Lim, C. Du, H. Shi, C. Wang, X. Luo; "Influence of V-shaped plasmonic nanostructures on beam propagation"; Appl. Phys. B 86, 461-466 (2007).
"New Superlensing Technique Brings Everything into Focus"; Scientific American.com; News, Jul. 12, 2007.
R.Merlin, et al.; "Radiationless Electromagnetic Interference: Evanescent-Field Lenses and Perfect Focusing"; Science AAAS 317, 927 (2007).
Y. Fu, W. Zhou, L. Lim; "Geometrical characterization issues of plasmonic nanostructures with depth-tuned grooves for beam shaping"; Optical Engineering; vol. 45(10), 108001 (Oct. 2006).

* cited by examiner

*Primary Examiner*—Kiet T Nguyen
(74) *Attorney, Agent, or Firm*—Bracewell & Giuliani LLP (57) ABSTRACT

A surface plasmonic polariton lens is disclosed that has an optical plate having incident thereupon waves of electromagnetic radiation. The plate also has a thin metal film of a metal having a negative permittivity. There are slits in the thin film, the slits being of decreasing radial width, and decreasing radial separation at increasing radius and being for the transmission therethrough of diffracted waves of the electromagnetic radiation. There are rings between the slits, the rings being of decreasing radial width at increasing radius and being for the transmission therethrough of evanescent waves of the electromagnetic radiation. The diffracted waves and the evanescent waves form propagated waves. A probe with such a lens, and an inspection apparatus and method using the probe are also disclosed.

31 Claims, 4 Drawing Sheets

PLASMONIC STRUCTURE LENS AND ITS APPLICATION FOR ONLINE INSPECTION

TECHNICAL FIELD

This invention relates to a plasmonic structure lens and particularly, though not exclusively, to a plasmonic nanostructure-based super lens; as well as to its application for online inspection, particularly where the application is for online inspection in nano-metrology applications.

BACKGROUND

Surface plasma polariton ("SPP") metallic nanostructures flanked with periodic corrugations on the exit side, or on both sides, of a metallic thin film have been investigated for super imaging. Enhancement of transmission is derived by the plasmonic nanostructures. Beam shaping may be achieved by using the nanostructures so that it can be used as a super-lens for nano-focusing. However, to realize a true far-field super-resolution imaging and/or focusing a special coupling mechanism is needed to convert a large band of the enhanced evanescent waves, or SPP wave, to propagating waves in free space.

Surface plasmon polaritons are collective electronic excitations, or charge density waves. They are characterized by intense electromagnetic fields confined to the surface. They have many uses. For instance, an SPP wave can boost the transmission of light through sub-wavelength hole-arrays in metal films. However, its near-field signal is too weak to be collected by conventional far-field optical systems, and the limited propagation depth (within several tens of nanometers only) limits its application and further development. SPP-based systems may be used in data storage, semiconductors, near-field scanning microscopy, biomedical and sensing. However, for this to be the case the weak near-field signal problem must first be overcome.

Diffractive elements may work at near field in scanning near-field optical microscope systems to replace conventional optical fiber probes. However, controlling the constant working distance between the planar diffractive element and sample surface is difficult in practice.

For conventional zone plates working in the far-field region, resolution (Rayleigh criterion for resolution) of two point sources by a zone plate or resolving power is determined that for N<200, the limit of resolution is greater than that of a lens with the same aperture diameter D, if the zones which contribute light with a positive phase to the observation point are used, and less than that of the lens if the zones which contribute light with a negative phase to the observation point are used. Resolution on the axis is diffraction limited. It approaches the Rayleigh limit when the number of zones exceeds about 100 by which the outer diameter of the zone plate will increase significantly. The focal length of a given zone plate is determined by the incident wavelength.

An enhanced localized surface plasmon polariton ("LSPP") based optical probe working at short wavelengths has been proposed. Such a probe may have high spatial resolution (up to 50 nm) compared with that of an optical interferometer. It is therefore possible to conduct surface measurements at much higher speeds than when using a scanning probe microscope. Scattering and field localization can be excited by metallic nanostructures within nanometer scales of distance of the sample surface. The localization and enhancement of the electromagnetic field by plasmon coupling to a metallic nanostructure may cause amplified transmission and intensity in a local region at a nanometer scale. The enhanced transmission may be derived due to the coupling of a photon to an SPP on one side of the metal, subsequent tunneling of the SPP through the nanostructures (holes or slits) to establish an SPP at the other side, and the final re-radiation into a photon. One way to couple free propagating light to surface plasmons is to have a periodic structure on the surface to satisfy conservation of energy and momentum. Therefore, a single aperture surrounded by a periodic corrugation in the metal surface will also display an enhanced transmission by the surface plasmon. As such, the near-field signal is amplified via coupling of the enhanced SPP effect in the nanostructure. The nanostructure and its related parameters depend on the application. Such a nanostructure can be termed as "nano-lens" or "super-lens"

It has been reported that the transmission and intensity of an SPP may be increased for a metallic thin film with a prescribed nanostructure. Propagation depth of the enhanced SPP can reach as long as 20 µm for the metallic thin film at a wavelength of 500 nm. Fabrication of the nanostructure may be by the use of focused ion beam direct milling. It has the advantages of high resolution, localized scanning, and one-step fabrication. Both material removal and deposition can be carried out using the focused ion beam.

Optical nano-metrology and instruments are widely used in the data storage and semiconductor industries. Commonly used apparatus and methods include optical interferometers and scanning probe microscopy. However, spatial resolution of optical interferometers does not satisfy the needs of industry as it cannot detect a feature size less than 100 nm due to the well-known limitations of diffraction. Scanning probe microscopy can increase the spatial resolution, but the measurement speed is slow and may fail to meet the requirement of mass production due to its point-by-point scanning mode. Therefore, sampling examination has been adopted to measure nano-particles of individual devices, or parts, by use of scanning probe microscopy.

Present near field imaging tools have near-field detection methods that are generally point-by-point scanning. Hence they are very slow in probing and need a relatively long time to acquire images due to the greater scanning time. Also, the probe needs to be changed often due to wear when working on irregular surfaces. Finally, the probe is easily contaminated during scanning.

SUMMARY

According to a first exemplary aspect there is provided a surface plasmonic polariton lens. The surface plasmonic polariton lens has an optical plate having a first planar surface and a second planar surface opposite the first planar surface. The first planar surface is adapted to have incident thereupon waves of electromagnetic radiation. A thin metal film is provided on the second planar surface, the thin film being of a metal having a negative permittivity. There are slits in the thin film. The slits are of decreasing radial width, and decreasing radial separation at increasing radius. The slits are for the transmission therethrough of diffracted waves of the electromagnetic radiation. There are rings between the slits. The rings are of decreasing radial width at increasing radius. The rings are for the transmission therethrough of evanescent waves of the electromagnetic radiation. The diffracted waves and the evanescent waves form propagated waves.

The electromagnetic radiation may be light. The light may have a wavelength in the range from ultra violet to infrared. The light may be at a wavelength of 633 nm. The slits may be concentric and/or circular. The slits may be of a radial width less than a wavelength λ of the electromagnetic radiation. The lens may have a focal length in the range of 0.1λ to 10λ. The rings may be concentric and/or circular. The slits may be substantially V-shaped. The rings may be substantially shaped like an inverted V. The optical plate may be composed of optical glass and/or quartz. There may be no more than ten slits. The diffracted waves and the evanescent waves may combine by interference to form the propagated waves. An outermost slit of the slits may have a diameter of less than 20 μm. The metal may be gold, silver, chromium, aluminum, copper, or nickel. The thin layer of metal may be of a thickness in the range 100 nm to 400 nm. The thin layer of metal may be of a thickness of 300 nm.

The surface plasmonic polariton lens as claimed in claim 1 incorporated in a probe, the probe further comprising a body having an opening therethrough in which the surface plasmonic polariton lens is mounted, a probe holder, and an optical fiber mounted in the holder; the surface plasmonic polariton lens and a facet of the optical fiber being spaced apart at a lower surface of the body and being aligned with each other.

According to a second exemplary aspect there is provided apparatus for inspection of a sample. The apparatus has a probe as described above, a laser as a source of light, and a laser Doppler interferometry system.

The apparatus of the second exemplary aspect may further comprise a white light source. The probe may be connected to a three-dimensional nano-stage mounted on an anti-vibration table. The apparatus may further comprise an optical fiber sensor. The optical fibre sensor may comprise the optical fiber mounted in the probe holder, the three-dimensional nano-stage, an analog/digital converter, and a computer for maintaining a constant working distance between the sample and the probe. The laser Doppler interferometer system may comprise a first frequency modulator operatively connected to a first polarizing beam splitter. A first output from the first polarizing beam splitter may be operatively connected to a phase-meter and lock-in phase amplifier. A second output from the first polarizing beam splitter may be operatively connected to a collimator lens. The output of the collimator lens may be operatively connected to a first polarizer. The laser Doppler interferometer system may be a laser Doppler heterodyne interferometer system. The laser Doppler heterodyne interferometer system may further comprise a second polarizing beam splitter for receiving an output from the first polarizer. A first output from the second polarizing beam splitter may be for reflection by a mirror and being passed to the photodetector and lock-in amplifier as an interference signal. A second output from the second polarizing beam splitter may be operatively connected to a second polarizer then an objective lens. An output of the objective lens may be for passing through the surface plasmonic polariton lens of the probe and onto the sample. The apparatus may further comprise a control for maintaining the working distance. The control may be a feedback servo-control, a closed-loop control, or an open-loop control.

According to a third exemplary aspect there is provided a method for inspection of a sample. The method includes using a probe as described above for improving lateral resolution, focusing and location adjustment of a sample; and using a laser Doppler interferometry method for dynamic online inspection.

For the third exemplary aspect the laser Doppler interferometry method may be a laser Doppler heterodyne interferometry method. A constant working distance may be maintained by use of an optical fiber sensor. The laser Doppler heterodyne interferometry method may include modulating a laser beam and splitting the modulated laser beam to form a first output beam and a second output beam. The first output beam may be passed to a phase-meter and lock-in phase amplifier. The second output beam may be collimated then polarized. The second output beam may be subsequently split by polarization to give a first polarized output beam and a second polarized output beam. The first polarized output beam may be reflected from the sample surface then passed to the photodetector and lock-in amplifier as an interference signal, and subjected to signal processing. The second polarized output beam may be again polarized then passed through an objective tens. The output beam from the objective lens may be passed through the surface plasmonic polariton lens of the probe and onto the sample. The sample may modulate the beam. The modulated beam may be passed through the surface plasmonic polariton lens of the probe in a reverse direction, the objective lens, the second polarizer, the second beam splitter and to the photodetector and lock-in amplifier, and subjected to signal processing.

BRIEF DESCRIPTION OF THE DRAWINGS

In order that the invention may be fully understood and readily put into practical effect, there shall now be described exemplary embodiments, the description being by way of non-limitative example only and being with reference to the accompanying illustrative drawings.

In the drawings.

DETAILED DESCRIPTION OF EXEMPLARY EMBODIMENTS

By use of the enhanced localized surface plasmon polariton super-lens for nano-metrology, it may be possible to enhance the measurement speed and spatial resolution. As such, such an LSPP super-lens may be useful for measurement at the nano scale of surface defects on, for example, magnetic sliders, hard disks, and semiconductor wafers. It may also be used for biomedical single cell/molecular in vitro detection and analysis.

Figure 1:
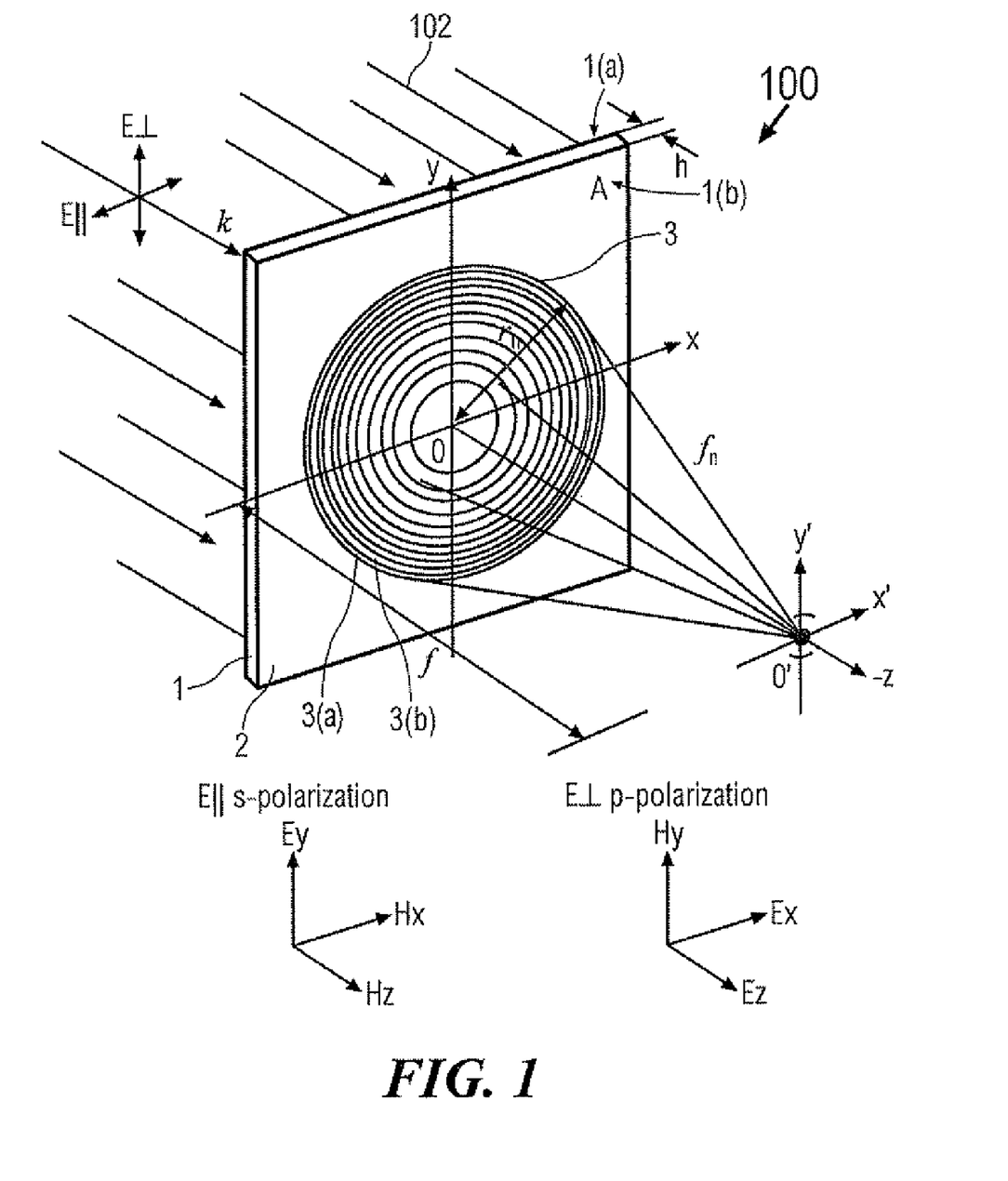
FIG. 1 is an illustration of an exemplary embodiment of a surface plasmon polaritons-based symmetrical nanostructure forming a super-lens.

FIGS. 1 to 6 show an exemplary embodiment of an enhanced SPP-based symmetrical nanostructure. It is a plasmonic micro-zone plate ("PMZP") 100 comprising a plate 1 of optical glass or quartz, and a thin film 2 of a metal. The metal thin film 2 may be formed by coating using vapor phase deposition, vacuum evaporation, liquid phase deposition, electroplating, ion sputtering, or any combination thereof. The PMZP 100 is for the purpose of super-focusing with a focal length f. The plate 1 has a first planar surface 1(*a*) that is illuminated by a plane wave 102 of electromagnetic radiation. The electromagnetic radiation 102 may be in the UV to infrared wavelengths and is preferably light from a laser. The light may have a wavelength of 633 nm. A second planar surface 1(*b*) of the plate 1 is opposite the first surface 1(*a*) and is coated with the thin film 2 of a metal with a negative permittivity. The metal may be a noble metal such as gold or silver. It may also be, for example, nickel, chromium or aluminum. The film 2 may be of any suitable thickness but is preferably in the range 100 nm to 400 nm, and more preferably is 300 nm. As illustrated, the film 2 is of silver (Ag). The film 2 has a refractive index of:

$$n+ik=-4.153-1.034i$$

and a permittivity of $$\epsilon=(n+ik)^2=-17.244+0.498i$$

for a light with a wavelength in a vacuum of $\lambda_0=633$ nm. The linear polarization state of the incident waves, denoted by $E_\parallel$, and $E_\perp$, indicates the incident E-field's direction. The relevant E- and H-field components for the two polarization states are also shown.

The thin film 2 is between air and the plate 1. For an evanescent wave with given $k_x$, we have:

$$k_{zj}=+[\epsilon_j(\omega/c)^2-k_x^2]^{1/2} \text{ for } j=1 \text{(air) and } j=3 \text{ (glass); and}$$

$$k_{zj}=+i[k_x^2-\epsilon_j(\omega/c)^2]^{1/2} \text{ for } j=2 \text{ (Ag film).}$$

Super-focusing requires regenerating the evanescent waves. Thus the super-lens should be operated with the condition:

$$|k_{z1}\epsilon_1+k_{z2}\epsilon_2||k_{z2}/\epsilon_2+k_{z3}/\epsilon_3|\rightarrow 0.$$

Physically, this would require exciting a surface plasmon at either the first surface 1(*a*) or the second surface 1(*b*). For $E_\perp$ waves, a negative permittivity is sufficient for focusing evanescent waves. Because electric permittivity $\epsilon<0$ occurs naturally in silver and other noble metals at visible wavelengths, a thin metallic film can act as an optical super-lens. In the electrostatic limit, the $E_\perp$ wave dependence on $\mu$ is eliminated and only E is relevant.

Figure 5:
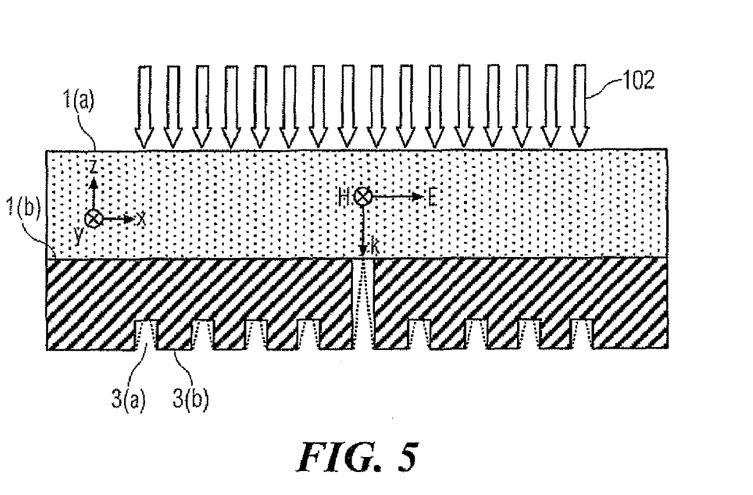
FIG. 5 is a cross-sectional view on an enlarged scale showing the slits and rings of FIG. 1.
Figure 6:
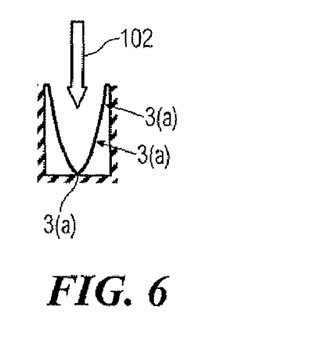
FIG. 6 is a cross-sectional view on an enlarged scale showing one slit of FIG. 5.

The film 2 has a zone plate structure 3 comprising a series of concentric, circular slits 3(*a*) into the film 2. The slits 3(*a*) may be other than concentric and thus may be eccentric, and may be other than circular. For example, the slits 3(*a*) may be elliptical and/or in the form of multiple micro/nano-pinholes distributed around the innermost slit. The slits 3(*a*) may be other than thoroughly penetrated grooves. The innermost slit passes completely through the film 2 to expose the plate 1 beneath, with the depth of the slit 3(*a*) decreasing as the radius increases. In addition, the slits 3(*a*) decrease in radial width as the radius increases, and the spacing of the slits 3(*a*) also decreases as the radius increases. Each slit 3(*a*) constitutes a zone. The number of slits 3(*a*) is preferably less than ten. Preferably, the slits 3(*a*) are approximately rectangular or V-shaped. This therefore forms concentric circular rings 3(*b*) of film 2 between the slits 3(*a*). The rings 3(*b*) may be other than concentric and thus may be eccentric, and may be other than circular. For example, the rings 3(*b*) may be elliptical. Consequently, the rings 3(*b*) are of decreasing radial width with increasing radius, and their spacing also decreases with increasing radius. Furthermore, it is preferred for the rings to be shaped to approximate a rectangle or an inverted V.

Super focusing takes place by interference of the localized SPP waves which exit from strips 3(*b*) and the diffraction wave from the slits 3(*a*). Diffraction and interference contribute to the transition from the evanescent waves to the propagation wave in the quasi-far-field region (i.e. in the range $\sim 0.1\lambda$ to $\sim 10\lambda$. The transition makes super-focusing with a longer focal length possible at and near the quasi-far-field with lateral resolution beyond the diffraction limit. The focal length may be in the range $\sim 1.0\lambda$ to $\sim 10\lambda$.

The SPP wave is a special kind of electromagnetic field. It can propagate along the two surfaces of film 2 but is bound to the film 2 and will not radiate from the film 2. Considering the two surfaces of the film 2, the SPP wave of each surface will be coupled and propagate in the form of a cavity mode (controlled by the depth of the grooves), mainly for p polarization (E field is perpendicular to the indentation geometry plane). The electromagnetic wave has plasmon excitation and allows high transmission with very small widths of slits 3(*a*).

Super-focusing of the super lens 100 will take place when the SPP wave is converted into propagation waves through zone diffraction and interference. When the p-polarized incident plane wave (also known as the TM mode) impinges the entrance to a slit 3(*a*), it will excite SPP wave. The SPP wave couples with the incident wave and propagates along the slits 3(*a*) until they reach the exit of the slit 3(*a*) where the coupled waves radiate into the beam in free space.

The thickness of the film 2 will affect excitation and coupling of the SPP wave. The traditional approach to SPP wave coupling and propagating in slit waveguide mode is that the enhancement factor of transmission rapidly grows with increasing film thickness up to 50 nm. Above 50 nm, the enhancement is sharply suppressed due to the intrinsic loss inside the Ag film, so that the transmissivity decays as film thickness further increases. In the exemplary embodiment of FIG. 1, the film 2 is of a thickness in the range 200 nm to 400 nm, but is more preferably 300 nm. By having the film 2 of such a thickness will enable working in groove cavity mode and to obtain an improved focusing performance.

In FIG. 1 a plane wave propagates along the z axis. The vacuum wavelength of the light, $\lambda_0=633$ nm, is in the visible regime ($v=c/\lambda_0=474.34$ THz). The dielectric constant used for silver at this wavelength is $\epsilon=-17.244+0.498i$, and the corresponding refractive index is $n=-4.153-1.034i$. The film 2 has a thickness $h_{Ag}$. Maxwell's equation is decoupled into $E_\parallel$ and $E_\perp$ modes, as indicated in FIG. 1. The $E_\parallel$ mode consists of $E_y$, $H_x$, and $H_z$ field components (s-polarization). The $E_\perp$ mode consists of $E_x$, $H_y$ and $E_z$ field components (p-polarization). By analyzing the field distributions in the near-field of the exit plane (surface 1(*b*)) it is possible to investigate the transmission of the PMZP 100. The polarization state ($E_\parallel$ and $E_\perp$), Ag film thickness, and designed focal length of the PMZP 100 are used as variable parameters to study the corresponding variations in the transmission and focusing performance of the PMZP 100 with negative zones/slits 3(*a*). For example, a PMZP 100 can have parameters of focal length f=1 μm, and outer diameter of the zones/slits 3(*a*) OD=11.93 μm.

Focusing is by interference between the SPP wave and the diffraction waves from the zones 3(*a*). The interference can exist within a coherence length Lc of the "source," but not beyond it. The source is equivalent to a source with central wavelength of $\lambda_{in}=633$ nm and bandwidth of $\Delta\lambda=\lambda_{in}-\lambda_{SP}$, and thus DOF$\leq$Lc, where Lc=$\lambda^2/(\lambda_{in}-\lambda_{SP})$. For the SPP interference, the wave vector $k_x$ of the incident optical wave projected on the plane parallel to the surface of the film 2 must equal $k_{SP}$. We define the focal length as $f_{PMZP}=f_{FZP}+\Delta$, where $\Delta$ is the SPP-related compensation factor. This means that a feedback control system is immune for the auto-focusing system with probe scanning while keeping a constant working distance, provided that flatness variation of sample substrate is within the range of the DOF. In addition, a series of focal points, behind and in front, at distances $\pm f/2(n+1)$ from the plate, where $n=0, 1, 2, \ldots$, corresponding to its odd-order diffraction patterns along the z direction, $f/3, f/5, f/7, \ldots$, for the conventional zone plates, were not found in our exampled PMZP 100. In addition, the focused beam spot size for the PMZP 100 with four designed focal lengths is not limited by the Rayleigh criteria. Also, the spot size of the PMZP 100 is a function of incident wavelength, SPP wave, focal length, numerical aperture, and film thickness.

Figure 2:
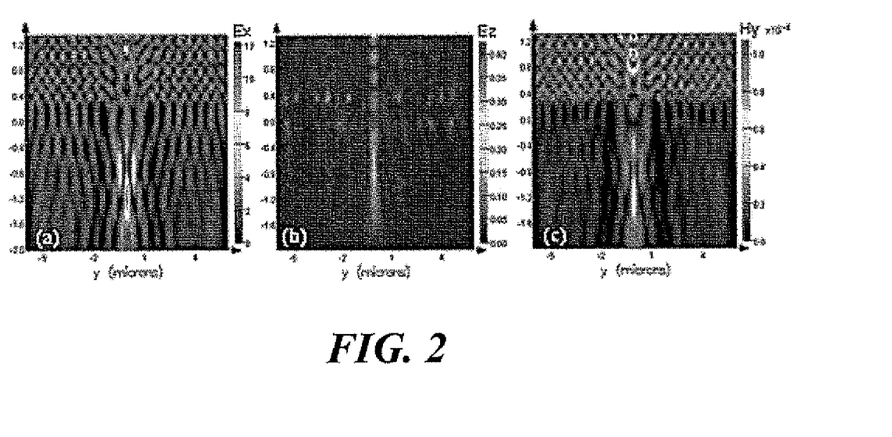
FIG. 2 shows the electromagnetic field distribution of the embodiment of FIG. 1 in the y-z plane for components of ($a$) $|E_x|^2$, ($b$) $|E_z|^2$ and ($c$) $|H_y|^2$ in p-polarization.

FIG. 2 shows electromagnetic field distribution in y-z plane for components of (a) $|E_x|^2$; (b) $|E_z|^2$; (c) $|H_y|^2$, for the PMZP 100 in TM mode. Designed focal length and film 2 thickness of the PMZP 100 are 1 μm and 300 nm, respectively. The incident beam after the PMZP 100 can be focused as small as ~220 nm at y-z plane on the line of $z=-1.25$ μm. The spot size can be further reduced by means of optimization of the geometrical parameters of the zone plate structure 3. The results demonstrate that the transmission is greatly enhanced after exit from the PMZP 100.

Figure 3:
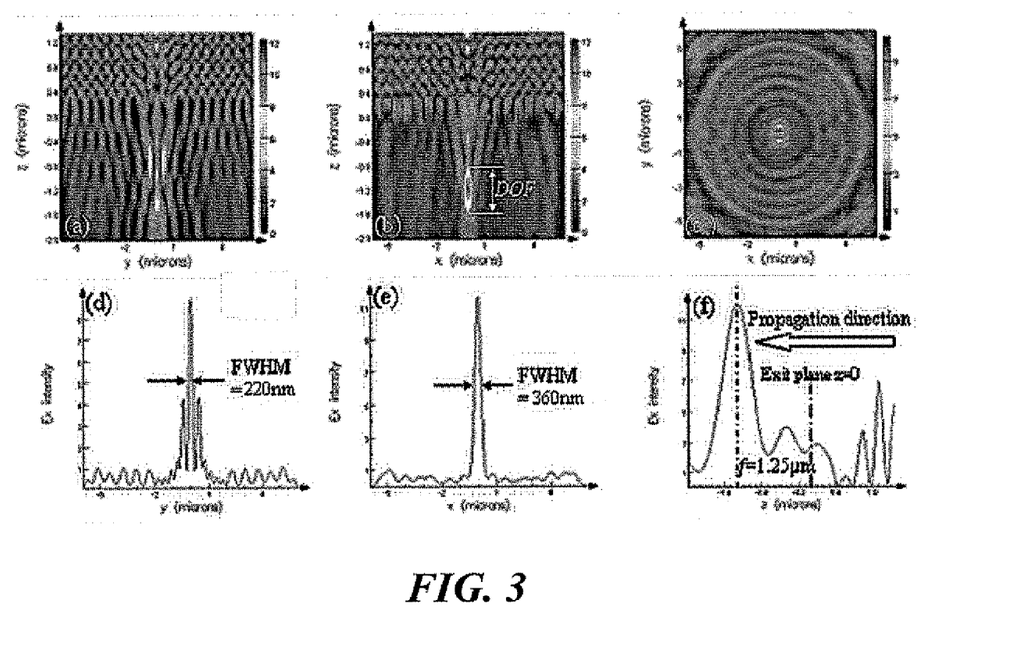
FIG. 3 is six representations of results of the exemplary embodiment of FIG. 1 being electric field intensity in ($a$) the y-z plane, ($b$) the x-z plane and ($c$) the x-y plane, and electric field transmission in ($d$) the x-z plane, ($e$) the y-z plane and ($f$) the x-y plane.

FIG. 3 is an example of a plasmonic micro-zone plate (negative) with outer diameter, Ag film thickness, and working wavelength of 11.93 μm, 300 nm, and 633 nm, respectively. The electric field distribution results were calculated using the finite-difference and time-domain ("FDTD") algorithm. The propagation direction is the z axis. The electric field intensity $|E_x|^2$ with TM polarization ($H_x=H_z=0$) incidence is shown in the:

(a) y-z plane;
(b) x-z plane; and
(c) x-y plane.

The electric field transmission with TM polarization ($H_x=H_z=0$) incidence in line $z=-1.25$ μm (calculated focal plane) is shown in:

(d) x-z plane, y=0;
(e) y-z plane, x=0; and
(f) x-y plane, z=0.

The designed focal length, and outmost zone/slit diameter using scalar theory is f=1 μm, and 53 nm, respectively. Calculated depth of focus (DOF) is ~700 nm (scalar theory designed value is 8.85 nm). The site of z=0 is the exit plane of the film 2.

From FIG. 3 it can be seen that the transmission is enhanced. The side lobe of the intensity distribution at the y-z plane is ~40% and is higher than at the x-z plane. It can be attributed to the SPP-caused enhancement of transmission in the y axis, as shown in FIG. 2(c). It can be seen from FIG. 3 that the sub-wavelength focusing spot size is already beyond the diffraction limit. Electric intensity is enhanced to four orders of magnitude in comparison to that of the TE mode transmission. The calculated focal length and depth of focus ("DOF") is longer than that of designed values, especially for the DOF. The difference of the DOF between the designed value and calculated value is a factor of almost 90. Transmission with the $E_\perp$ wave illumination is enhanced due to the excited SPP wave coupling which is then converted to propagation wave by diffraction. FIG. 3(f) shows that there is only one peak transmission after exit plane of the film 2. Furthermore, Fabry-Pérot-like phenomenon is found through the central aperture during the SPP wave coupling and propagation in the cavity mode, as shown in FIGS. 3(a), (b) and (f). It plays a positive role for the enhanced transmission.

Figure 4:
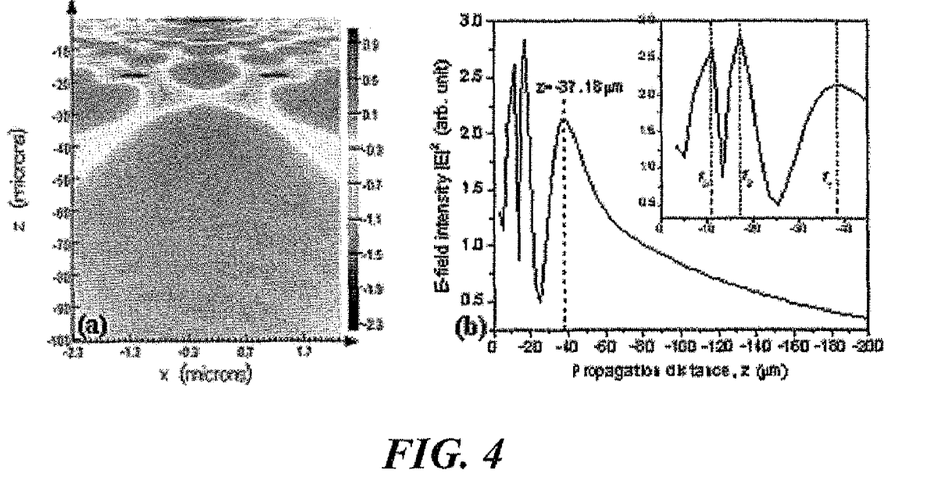
FIG. 4 is ($a$) an image and ($b$) a graph that show the far-field electric field intensity $|E|^2=|E_x|^2+|E_y|^2+|E_z|^2$ distribution in x-z plane at y=0.

FIG. 4 presents far-field electric field intensity $|E|^2=|E_x|^2+|E_y|^2+|E_z|^2$ distribution in x-z plane at y=0:

(a) logarithmic $|E|^2$ in x-z plane; and
(b) $|E|^2$ v propagation distance z for the PMZP 100 in the far-field region.

The designed focal length f and film 2 thickness of the PMZP 100 are 1 μm and 300 nm, respectively. Three peak transmissions at $z=-17.08$ μm, $z=-11.05$ μm, and $z=-37.18$ μm, are in the far-field. Numerical results show that no focal points are in the near-field. The distances are quite different from designed values obtained using the conventional equations:

$$r_n = (2n\lambda f_{FZP} + n^2\lambda^2)^{1/2} \text{ and}$$

$$f_{FZP} = R^2/\lambda,$$

where: $n=1, 2, 3, \ldots$, The phase difference of the PMZP is $2\pi$ instead of $\pi$ as it is for a conventional Fresnel zone plate. Therefore, it corresponds to optical path difference $\lambda$ between the two neighbored slits instead of $\lambda/2$ for that of the standard Fresnel zone plate.

$f_{FZP}$ is the designed principal focal length of Fresnel lens and given in terms of radius R of the inner ring and incident wavelength by $f_{FZP}=R^2/\lambda$, and R is the radius of the inner slit 3(a).

The focusing performance in the far-field is poor. In addition, an extra lower peak transmission is found at distance $z=-0.4$ μm.

Figure 7:
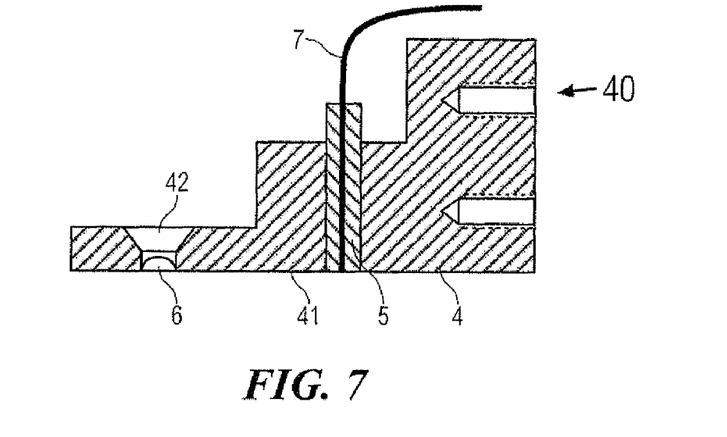
FIG. 7 is an exemplary embodiment of a probe utilizing the exemplary embodiment of a super-lens of FIGS. 1 to 6.

FIG. 7 shows a side view of an exemplary embodiment of a probe 40 including an exemplary embodiment of a super-lens. The probe 40 may be for use in an assembly for on-line inspection of nano-scale components. In this exemplary embodiment, there is a body 4, tube 5 preferably of metal, a super lens 6, and a multi-mode optical fiber 7 mounted in the tube 5. The body 4 has a funnel-shaped opening 42 therethrough in which the super-lens 6 is mounted. The opening 42 is funnel-shaped to avoid blocking the incident light beam from the objective lens 18. The super lens 6 and facet of the optical fiber 7 are spaced apart by a sufficient distance to avoiding cross talk between the super lens 6 and the facet of the optical fiber 7. For example, the spacing may be 5 mm. The super lens 6 and facet of the optical fiber 7 are at the same surface 41 and are preferably both level and aligned with to each other. As shown, they are both horizontal, but the body may be at any suitable inclination. The probe 40 does not require a constant working distance feedback control system when in an on-line inspection system with sub-wavelength resolution.

Figure 8:
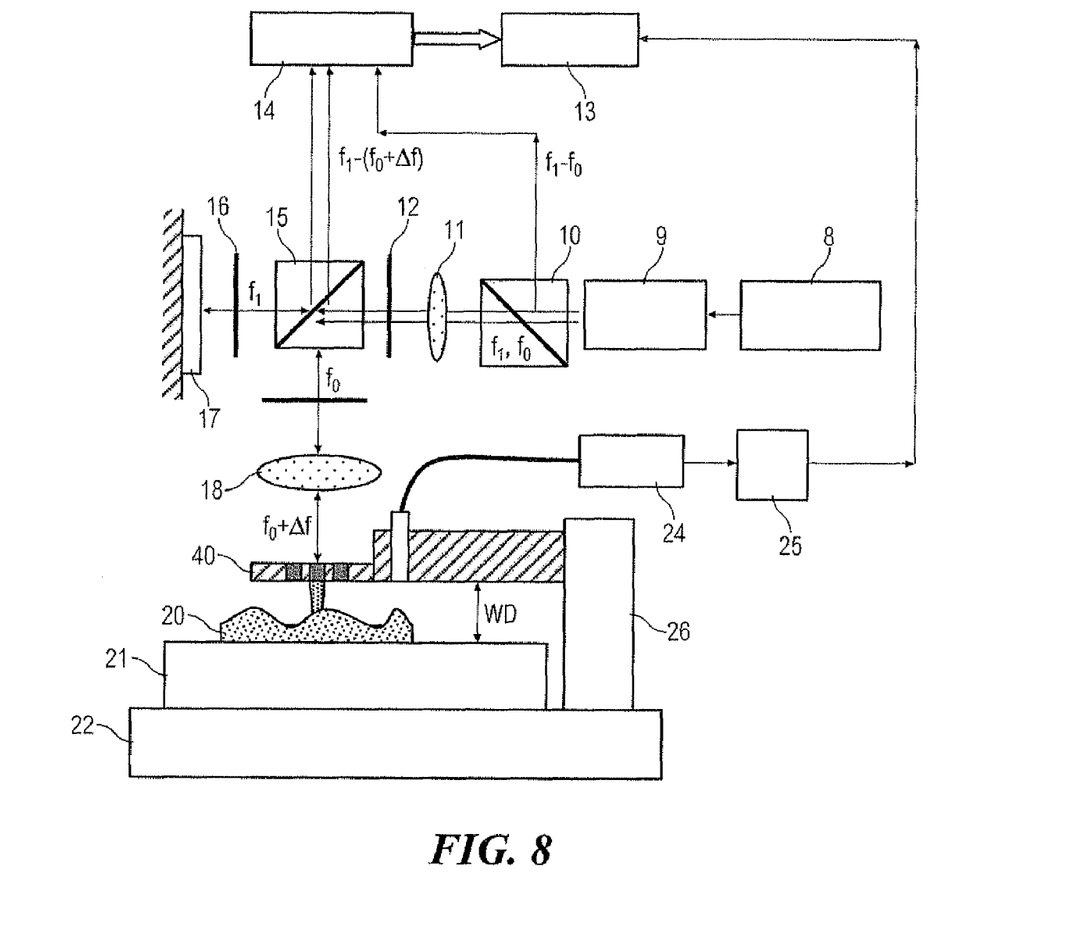
FIG. 8 is an exemplary embodiment of an inspection system using the exemplary embodiment of the probe of FIG. 7.

FIG. 8 is a schematic illustration of an on-line inspection system using the probe 40. The probe 40 is used to improve lateral resolution, focusing and location adjustment. A laser Doppler interferometry system is used for dynamic online inspection. The probe 40 is connected with a three-dimensional (3 D) nano-stage 26 that is preferably mounted on an anti-vibration table 22. A constant working distance (WD) is maintained by use of an optical fiber sensor 24 which comprises the multi-mode optical fiber 7 and tube 5, the 3 D nano-stage 26, an analog/digital converter 25, and computer 13. Either open loop or close-loop controlling can be employed in the system for the constant WD.

The laser Doppler interferometer system has a laser 8 heterodyne system. The laser beam $f_i$ is modulated in a frequency modulator 9 and split by polarization in a polarizing beam splitter 10. One output from the beam splitter 10 is $f_i-f_o$ and is passed to a phase-meter and lock-in phase amplifier 14. The remaining beam $f_o$ is collimated by being passed through collimator lens 11, then polarized in a polarizer 12. Further beam splitting by polarization takes place in a second polarizing beam splitter 15.

Output from second polarizing beam splitter 15 is a beam $f_i$ that is reflected by mirror 17 then passed to photodetector and lock-in amplifier 14 as an interference signal. It is then input into computer 13 for signal processing. Two photodetectors are required. One is for the object beam and reference mirror 17 beam; and the other for the light source modulated signal $f_i - f_o$. Another output from second polarizing beam splitter 15 is output beam $f_o$. This is polarized by being passed through polarizer 23, then passed through objective lens 18 to give $f_o$. This is passed through the PZMP 100 super-lens and on to the sample 20. Information of the whole sample 20 can be obtained by moving stage 21, or probe 19 along the radial direction while the sample 20 rotates. The optical PZMP 100 super-lens of probe 40 improves lateral resolution of the interference system from within diffraction limitation to beyond diffraction limitation.

The enhanced SPP wave passing through the nanostructure inside the probe 40 is modulated by the sample 20 surface to give Δf, and then reflected back to the objective lens 18 through the super-lens 6. Therefore, the beam twice passes through the super-lens 6—once in each direction. It is then passed through the objective lens in the reverse direction, and the second polarizer, again in the reverse direction. After passing through the second beam splitter it is passed to the photodetector and lock-in amplifier 14 and input into computer 13 for signal processing to transform the interference signal by a phase change, and then to derive a three-dimensional topography of the measured sample surface by data correlation and fitting. Known techniques may be used for the signal processing.

Inspection speed strongly depends on sample rotating speed, and response speed and dynamic range of the photodetectors 14. For a sample 20 with a surface feature of a height larger than the WD, a feedback servo-control (close-loop control) may be required. If the sample 20 has a surface feature of a height smaller than the WD, an open-loop control may be necessary for maintaining the WD constant.

The WD depends on designed and fabricated plasmonic nanostructure for beam focusing. The ideal case is that the beam spot size is as small as possible, and WD (focal length of the probe) is as large as possible.

Whilst the foregoing description has described exemplary embodiments, it will be understood by those skilled in the technology concerned that many variations in details of design, construction and/or operation may be made without departing from the present invention.

The invention claimed is:

1. A surface plasmonic polariton lens comprising:
    an optical plate having a first planar surface and a second planar surface opposite the first planar surface;
    the first planar surface being adapted to have incident thereupon waves of electromagnetic radiation;
    a thin metal film on the second planar surface, the thin film being of a metal having a negative permittivity;
    slits in the thin film, the slits being of decreasing radial width, and decreasing radial separation at increasing radius;
    the slits being for the transmission therethrough of diffracted waves of the electromagnetic radiation;
    rings between the slits, the rings being of decreasing radial width at increasing radius;
    the rings being for the transmission therethrough of evanescent waves of the electromagnetic radiation;
    the diffracted waves and the evanescent waves forming propagated waves.

2. The surface plasmonic polariton lens as claimed in claim 1, wherein the electromagnetic radiation is light with a wavelength in the range from ultra violet to infrared.

3. The surface plasmonic polariton lens as claimed in claim 2, wherein the light is at a wavelength of 633nm.

4. The surface plasmonic polariton lens as claimed in claim 1, wherein the slits are at least one of: concentric, and circular; and the slits are of a radial width less than a wavelength λ of the electromagnetic radiation.

5. The surface plasmonic polariton lens as claimed in claim 4, wherein the lens has a focal length in the range of 0.1λ to 10λ.

6. The surface plasmonic polariton lens as claimed in claim 1, wherein the rings are at least one of: concentric, and circular.

7. The surface plasmonic polariton lens as claimed in claim 1, wherein the slits are substantially V-shaped; and the rings are substantially shaped like an inverted V.

8. The surface plasmonic polariton lens as claimed in claim 1, wherein the optical plate is composed of a material selected from the group consisting of: optical glass and quartz.

9. The surface plasmonic polariton lens as claimed in claim 1, wherein there are no more than ten slits and the slits pass through the thin film.

10. The surface plasmonic polariton lens as claimed in claim 1, wherein the diffracted waves and the evanescent waves combine by interference to form the propagated waves.

11. The surface plasmonic polariton lens as claimed in claim 1, wherein an outermost slit of the slits has a diameter of less than 20 μm.

12. The surface plasmonic polariton lens as claimed in claim 1, wherein the metal is selected from the group consisting of: gold, silver, chromium, aluminum, copper, and nickel.

13. The surface plasmonic polariton lens as claimed in claim 11, wherein the thin layer of metal is of a thickness in the range 100 nm to 400 nm.

14. The surface plasmonic polariton lens as claimed in claim 12, wherein thin layer of metal is of a thickness of 300 nm.

15. The surface plasmonic polariton lens as claimed in claim 1 incorporated in a probe, the probe further comprising a body having an opening therethrough in which the surface plasmonic polariton lens is mounted, a probe holder, and an optical fiber mounted in the holder; the surface plasmonic polariton lens and a facet of the optical fiber being spaced apart at a lower surface of the body and being aligned with each other.

16. Apparatus for inspection of a sample, the apparatus comprising:
    a probe as claimed in claim 15,
    a laser as a source of light, and
    a laser Doppler interferometry system.

17. Apparatus as claimed in claim 16 further comprising a white light source.

18. Apparatus as claimed in claim 16, wherein the probe is connected to a three-dimensional nano-stage mounted on an anti-vibration table.

19. Apparatus as claimed in claim 18, further comprising an optical fiber sensor; the optical fiber sensor comprising the optical fiber mounted in the probe holder, the three-dimensional nano-stage, an analog/digital converter, and a computer for maintaining a constant working distance between the sample and the probe.

20. Apparatus as claimed in claim 16, wherein the laser Doppler interferometer system comprises a first frequency modulator operatively connected to a first polarizing beam splitter; a first output from the first polarizing beam splitter being operatively connected to a phase-meter and lock-in phase amplifier; a second output from the first polarizing beam splitter being operatively connected to a collimator lens, the output of the collimator lens being operatively connected to a first polarizer.

21. Apparatus as claimed in claim 20, wherein the laser Doppler interferometer system is a laser Doppler heterodyne interferometer system.

22. Apparatus as claimed in claim 21, wherein the laser Doppler heterodyne interferometer system further comprises a second polarizing beam splitter for receiving an output from the first polarizer; a first output from the second polarizing beam splitter being for reflection by a mirror and being passed to a photodetector and lock-in amplifier as an interference signal.

23. Apparatus as claimed in claim 22, wherein a second output from the second polarizing beam splitter is operatively connected to a second polarizer then an objective lens; an output of the objective lens being for passing through the surface plasmonic polariton lens of the probe and onto the sample.

24. Apparatus as claimed in claim 23 further comprising a control for maintaining the working distance, the control being selected from the group consisting of: a feedback servo-control, a closed-loop control, and an open-loop control.

25. A method for inspection of a sample, the method comprising using a probe as claimed in claim 15 for improving lateral resolution, focusing and location adjustment of a sample; and using a laser Doppler interferometry method for dynamic online inspection.

26. A method for inspection as claimed in claim 25, wherein the laser Doppler interferometry method is a laser Doppler heterodyne interferometry method.

27. A method for inspection as claimed in claim 25, wherein a constant working distance is maintained by use of an optical fiber sensor.

28. A method for inspection as claimed in claim 26, wherein the laser Doppler heterodyne interferometry method comprises: modulating a laser beam and splitting the modulated laser beam to form a first output beam and a second output beam; the first output beam being passed to a phase-meter and lock-in phase amplifier and the second output beam being collimated then polarized.

29. A method for inspection as claimed in claim 28, wherein the second output beam is subsequently split by polarization to give a first polarized output beam and a second polarized output beam, the first polarized output beam being reflected from the sample surface then passed to a photodetector and lock-in amplifier as an interference signal, and subjected to signal processing.

30. A method for inspection as claimed in claim 29, wherein the second polarized output beam is again polarized then passed through an objective lens; the output beam from the objective lens being passed through the surface plasmonic polariton lens of the probe and onto the sample.

31. A method for inspection as claimed in claim 30, wherein the sample modulates the beam and the modulated beam is passed through the surface plasmonic polariton lens of the probe in a reverse direction, the objective lens, the second polarizer, the second beam splitter and to the photodetector and lock-in amplifier, and subjected to signal processing.

* * * * *